United States Patent [19]

Mais et al.

[11] Patent Number: 5,095,157
[45] Date of Patent: Mar. 10, 1992

[54] PROCESS FOR THE PREPARATION OF 2-CHLORO-4-NITRO-ALKYLBENZENE

[75] Inventors: Franz-Josef Mais, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 518,063

[22] Filed: May 2, 1990

[30] Foreign Application Priority Data

May 23, 1989 [DE] Fed. Rep. of Germany ....... 3916664

[51] Int. Cl.$^5$ ............................................. C07C 205/12
[52] U.S. Cl. .................................. 568/940; 568/937; 568/939; 570/207; 570/209
[58] Field of Search ....................... 568/937, 939, 940; 570/207, 209

[56] References Cited

U.S. PATENT DOCUMENTS

| | | | |
|---|---|---|---|
| 3,005,031 | 10/1961 | Friedrich | 260/646 |
| 4,031,147 | 6/1977 | Graham | 570/209 |
| 4,069,263 | 1/1978 | Lin | 570/209 |
| 4,069,264 | 1/1978 | Lin | 570/209 |
| 4,190,609 | 2/1980 | Lin | 570/209 |
| 4,289,916 | 9/1981 | Nakayama et al. | 570/209 |
| 4,647,709 | 3/1987 | Wolfram | 570/209 |
| 4,851,596 | 7/1989 | Mais et al. | 570/209 |
| 4,925,994 | 5/1990 | Mais et al. | 570/207 X |

OTHER PUBLICATIONS

Streitwieser, Jr. and Heathcock, 'Introduction to Organic Chemistry', 1985, pp. 669–670 (MacMillan Publishing Co.).

McMurry, Organic Chemistry, 'Organic Chemistry', 1985, pp. 506–507 (Brooks-Cole Publishing Co.).

Primary Examiner—Robert L. Stoll
Assistant Examiner—Chhaya Sayala
Attorney, Agent, or Firm—Sprung Horn Kramer & Woods

[57] ABSTRACT

In the preparation of 2-chloro-4-nitro-alkylbenzene by reaction of 4-nitro-alkylbenzene with elemental chlorine or chlorine-releasing compounds in the presence of a Friedel-Crafts catalyst in the liquid phase, particularly high selectivities in respect of the target compounds chlorinated exclusively in the 2-position are achieved if a dibenzo-condensed sulphur heterocycle of the formula

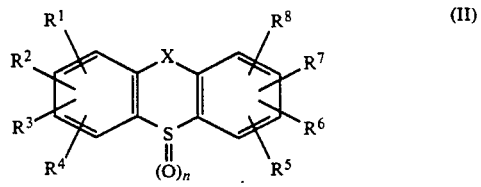

having the meanings given in the description for $R^1$ to $R^8$, X and n, is used as co-catalyst.

20 Claims, No Drawings

PROCESS FOR THE PREPARATION OF 2-CHLORO-4-NITRO-ALKYLBENZENE

BACKGROUND OF THE INVENTION

1. Field of the Invention

The invention relates to a process or the ring-monochlorination of 4-nitro-alkylbenzenes in the presence of Friedel-Crafts catalysts and simultaneous presence of sulphur-containing, benzo-condensed heterocyclic co-catalysts in the liquid phase.

2. Description of the Related Art

The reaction of 4-nitrotoluene with gaseous chlorine in the presence of Friedel-Crafts catalysts such as iron-III chloride (U.S. Pat. No. 3 341 595; J. Chem Soc. 1927, 2905) or antimony chlorides (Bull. Soc. Chim. Belg. 61 (1952), 317) is known. In addition to the desired 2-chloro-4-nitrotoluene, more highly chlorinated, positionally isomeric dichloro-4-nitrotoluenes and 4-nitrobenzyl chloride, as well as the ring-chlorinated derivatives derived from this, are observed as by-products.

Thus, a selectivity of about 92% for 2-chloro-4-nitrotoluene is observed when iron-III chloride is used as catalyst (see Example 2), which gave rise to the desire for further lowering, in particular of 2,6-dichloro-4-nitrotoluene and 4-nitro-benzyl chloride. It has been attempted further to increase the selectivity in the desired direction with the aid of co-catalysts. In this connection iron or iron-III chloride have particularly frequently been used with iodine as co-catalysts. In (Naturwiss. 17 (1929), 13; Houben-Weyl, Methoden der Organischen Chemie (Methods in Organic Chemistry), volume V/3 (1962), 704; JP-B-75/7589; CS 193 662). An iron/iodine/PCl$_3$ catalyst combination in the ratio by weight of 60:1:2 is disclosed in U.S. Pat. No. 3 005 031.

The selectivity for 2-chloro-4-nitrotoluene can indeed be increased to above 96% by the co-use of iodine (see Example 3), but this is at the cost of considerable difficulties. On the one hand the iodine introduced is discharged with the abundantly formed hydrogen chloride in the form of volatile compounds, for example as hydrogen iodide, which impairs the working up and the purity of the hydrochloric acid produced as by-product. Additionally, traces of iodine in the bound form, which cannot be removed by physical separation methods, remain in the chlorination mixture and in the end product 2-chloro-4-nitrotoluene. These impurities interfere considerably in the further processing of the distilled 2-chloro-4-nitrotoluene also and therefore signify a considerable reduction in the product quality. When working up such chlorination mixtures by distillation elemental iodine can sublime in more distant parts of the distillation apparatus; additionally formation of iodine-containing working-up residues occurs, which is not very favourable.

A process disclosed in DE-OS 3 128 442 for the chlorination of 4-nitrotoluene using iodine as the sole catalyst in an amount of, for example, 1% by weight, relative to the starting material, shows the described disadvantages of the use of iodine to a particular degree because of the increased quantity. Additionally, in this last-mentioned process up to 75% of the chlorine introduced escapes unused from the reaction mixture; consequently an excess of up to 300% above the required amount of chlorine will be necessary before an industrially required conversion of, for example, more than 90% is achieved.

A further process for the chlorination of aromatic hydrocarbons, amongst which 4-nitrotoluene is also listed, is described in CA 1 176 654; this process is carried out in a mixture with 96.5% sulphuric acid (ratio by weight H$_2$SO$_4$:4-nitrotoluene=1:1.35) with or without addition of small amounts of Al$_2$O$_3$. Further composition of the chlorination mixture or of the yield are not given. However, processes using such amounts of sulphuric acid are extremely unfavourable technologically, because of the corrosion, and environmentally, because of the waste disposal. Additionally, in process engineering an aqueous working up to remove the sulphuric acid is required before any precision distillation.

There was therefore the desire to find catalyst systems to increase the selectivity for 2-chloro-4-nitroalkylbenzenes, i.e. to suppress the said undesired by-products, in particular the higher levels of chlorination, which do not possess the disadvantages described above. It was possible to achive this object in an extremely favourable manner by the combination of Friedel-Crafts catalysts with the dibenzo-condensed sulphur heterocycles described further below as co-catalysts.

SUMMARY OF THE INVENTION

Accordingly, the invention relates to a process for the preparation of 2-chloro-4-nitro-alkylbenzene of the formula

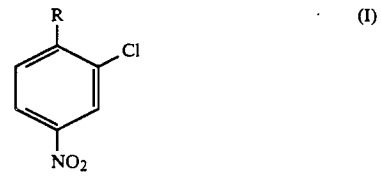

in which

R represents C$_1$–C$_4$-alkyl, by reaction of the 4-nitro-alkylbenzene on which the product is based with elemental chlorine or chlorine-releasing compounds in the presence of a Friedel-Crafts catalyst and a co-catalyst in the liquid phase, which is characterized in that the co-catalyst used is a dibenzo-condensed sulphur heterocycle of the formula

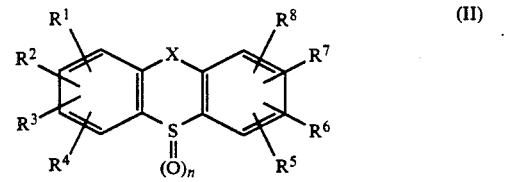

in which

R$^1$, R$^2$, R$^5$ and R$^6$ independently of one another denote hydrogen, halogen, hydroxy, cyano, nitro, amino, carboxyl, halogenocarbonyl, the sulphonic acid group, halogenosulphonyl, R$^9$, OR$^9$, SR$^9$, COR$^9$, OCOR$^9$, COOR$^9$, NHCOR$^9$, SCOR$^9$, SO$_2$R$^9$ or SO$_2$—OR$^9$, R$^9$ representing straight-chain or branched C$_1$–C$_8$-alkyl, C$_5$–C$_8$-cycloalkyl, C$_6$–C$_{12}$-aryl or C$_7$–C$_{10}$-aralkyl, R$^3$, R$^4$, R$^7$ and R$^8$ independently of one another and of the above radicals denote hydrogen, halogen or straight-chain or branched C$_1$–C$_8$-alkyl, or $C_1$–$C_8$-alkyl interrupted by the ether group —O— or by the ester groups —OCO— or —COO—, and additionally two adjacent radicals of $R^1$ to $R^4$ or of $R^5$ to $R^8$ can jointly form a fused ring, which can have 5 to 8 ring members and can be saturated, unsaturated, aromatic or, with the inclusion of one or two atoms from the group N, O and S, heterocyclic, and, furthermore, two adjacent radicals $R^1$ and $R^2$ or $R^5$ and $R^6$ can represent a dicarboxylic anhydride group, X represents —O—, —S—, —SO—, $SO_2$— or a single bond and n assumes the value zero or one.

DETAILED DESCRIPTION OF THE INVENTION

The dibenzo-condensed sulphur heterocycles of the formula (II) to be used according to the invention include the compound classes, which are indicated below merely by their through-numbered structure, comprising the phenoxathiins (III), the thianthrenes (IV), the thianthrene 5-oxides (V), the thianthrene 5,5-dioxides (VI), and the dibenzothiophenes (VII) with the index n having the meaning of zero, and the (unnumbered) compound classes comprising the phenoxathiin 10-oxides (VIII), the thianthrene 10-oxides (IX) identical to (V), the thianthrene 5,10-dioxides (X), the thianthrene 5,5,10-trioxides (XI) and the dibenzothiophene 5-oxides (XII), when the index n assumes the meaning one:

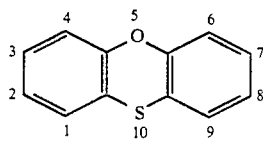
(III)

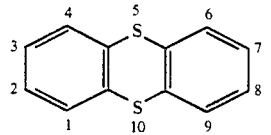
(IV)

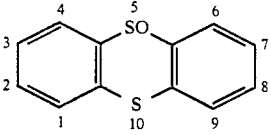
(V)

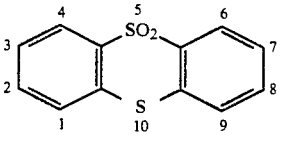
(VI)

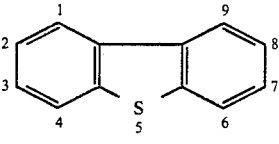
(VII)

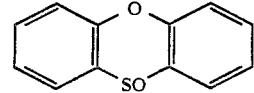
(VIII)

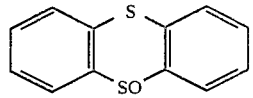
(IX)

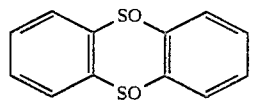
(X)

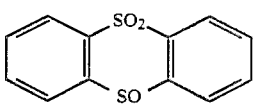
(XI)

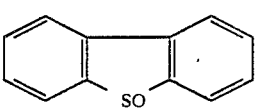
(XII)

Fluorine, chlorine, bromine or iodine, preferably fluorine, chlorine or bromine, and particularly preferentially chlorine or bromine may be mentioned as halogen. Fluorocarbonyl, chlorocarbonyl or bromocarbonyl, preferably chlorocarbonyl, may be mentioned as halogenocarbonyl. Fluorosulphonyl, chlorosulphonyl or bromosulphonyl, preferably chlorosulphonyl, may be mentioned as halogenosulphonyl.

Methyl, ethyl, propyl, isopropyl, butyl, isobutyl, tert.-butyl and the isomeric amyls, hexyls or octyls may be mentioned as straight-chain or branched $C_1$–$C_8$-alkyl. Preferred alkyl has 1–4, particularly preferred alkyl 1 or 2, C atoms.

$C_5$–$C_8$-Cycloalkyl is, for example, cyclopentyl, methyl-cyclopentyl, cyclohexyl, methyl-cyclohexyl, cycloheptyl or cyclooctyl, preferentially cyclopentyl or cyclohexyl.

$C_6$–$C_{12}$-Aryl is, for example, phenyl, naphthyl or biphenylyl, preferably phenyl.

$C_7$–$C_{10}$-Aralkyl is, for example, benzyl, phenylethyl, phenylpropyl or phenylbutyl, preferably benzyl.

$C_1$–$C_8$-Alkyl interrupted by the ether group —OR— or the ester groups —OCO— or —COO— is, for example, —$CH_2$— $OCH_3$, —$CH_2$—OCO—$CH_3$, —$CH_2$—CO—$OCH_3$ and the corresponding substituents in which —$CH_2$— or —$CH_3$ can be replaced to the stated extent by higher alkylene or alkyl groups.

Two adjacent radicals $R^1$ to $R^4$ or $R^5$ to $R^8$ on one or on both of the condensed benzene rings can jointly form a ring fused to such a benzene ring, which fused ring can contain 5 to 8 ring members and can be saturated, unsaturated, aromatic or heterocyclic, it being possible for fused heterocyclic rings to contain 1 or 2 atoms from the group N, O and S. Consequently, within the context of the compounds of the formula (II), a condensed benzene ring can be replaced, for example, by an indane structure, an indene structure, a tetralin structure, a naphthalene structure, a quinoline structure or another two-ring benzo-heterocyclic structure, the heterocyclic part of which can also be partially or completed hydrogenated, condensed with the aromatic part.

It is further possible that the two radicals $R^1$ and $R^2$ or $R^5$ and $R^6$, if they are adjacent, together represent a dicarboxylic anhydride group.

The said alkyl, cycloalkyl, aryl or aralkyl radicals can for their part be substituted, for example by methoxy, ethoxy, fluorine, chlorine, bromine, trichloromethyl, trifluoromethyl and, particularly in the aromatic parts, by nitro, hydroxy, amino or cyano.

Examples of the multitude of co-catalysts which can be used in accordance with the invention are listed below:
thianthrene,
2,7-dichlorothianthrene,
2-chlorothianthrene,
2,3,7,8-tetrachlorothianthrene,
1,2,3,4-tetrachlorothianthrene,
octachlorothianthrene,
2,8-dichlorothianthrene,
2,7-dibromothianthrene,
2,3,7-tribromothianthrene,
2,3,7,8-tetrabromothianthrene,
1-bromothianthrene,
2,3-difluorothianthrene,
2,7-difluorothianthrene,
2,8-difluorothianthrene,
2,3,7,8-tetrafluorothianthrene,
1,2,3,7,8,9-hexafluorothianthrene,
octafluorothianthrene,
2,7-diiodothianthrene,
2,7-dichloro-3,8-dibromothianthrene,
2,7-difluoro-3,8-dichlorothianthrene,
2-methyl-thianthrene,
2,7-dimethylthianthrene,
2,7-dimethyl-3,8-dichlorothianthrene,
2,8-dimethyl-3,7-dichlorothianthrene,
2,8-diethylthianthrene,
2,7-dimethyl-3,8-difluoro-1,9-dichlorothianthrene,
2-methyl-7-propylthianthrene,
2-hydroxy-1,3,7,8-tetrachlorothianthrene,
2-methoxy-1,7,8-trichlorothianthrene,
2,7-dimethoxythianthrene,
2,7-dimethoxy-3,8-dichlorothianthrene,
2,7-dibromo-3,8-dimethoxythianthrene,
2-methoxy-thianthrene,
1-ethoxythianthrene,
1-ethoxy-2,7-dichlorothianthrene,
2-(4-chlorophenyl)-3,7,8-trichlorothianthrene,
2-(4-methoxymethyl)-3-methyl-7,8-dichlorothianthrene,
2-methoxy-3,7-dichlorothianthrene,
2,7-bis(chloromethyl)-3-chlorothianthrene,
2,7-bis(trifluoromethyl)-thianthrene,
2,8-bis(trifluoromethyl)-thianthrene,
2,7-bis(trifluoromethyl)-3,8-dichlorothianthrene,
2-trifluoromethyl-7-cyano-1-methyl-3,8-dichlorothianthrene,
2-trichloromethyl-7-chloro-thianthrene,
2-benzyl-7-cyanothiahthrene,
2-benzyl-3,7,8-trichlorothianthrene,
2,7-dibenzylthianthrene,
2-methoxy-3-chloro-7,9-bis(trichloromethyl)-thianthrene,
2,7-bis[(methoxycarbonyl)methyl]thianthrene,
2,7-dichloro-3,8-bis[(methoxycarbonyl)methyl]thianthrene,
2,3-diphenylthianthrene,
2-phenyl-3,8-dichlorothianthrene,
2,7-diphenylthianthrene,
2,8-diphenylthianthrene,
2-phenyl-7-methyl-3,8-dichlorothianthrene,
2-(2-furyl)-thianthrene,
2-(2-thienyl)-3,7,8-trichlorothianthrene,
1-phenoxy-thianthrene,
1-phenoxy-3,7,8-trichlorothianthrene,
2,7-diphenoxythianthrene,
2-cyano-thianthrene,
2,7-dicyanothianthrene,
2,8-dicyanothianthrene,
2,3,7,8-tetracyanothianthrene,
2,7-dicyano-3,8-dichlorothianthrene,
2,7-dicyano-3,8-dichloro-1-methylthianthrene,
2-cyano-3,8-dibromo-thianthrene,
2-nitrothianthrene,
2,7-dinitrothianthrene,
2,8-dinitrothianthrene,
1,4-dinitrothianthrene,
1,9-dimethyl-4,6-dinitrothianthrene,
1,6-dimethyl-4,9-dinitrothianthrene,
1,9-dimethyl-4,6-dinitro-2-chlorothianthrene,
1,9-dimethyl-4,6-dinitro-2,8-dichlorothianthrene,
1,9-dimethyl-4,6-dinitro-2,3,7,8-tetrachlorothianthrene,
1,6-dimethyl-4,9-dinitro-2-chlorothianthrene,
1,6-dimethyl-4,9-dinitro-2,7-dichlorothianthrene,
1,6-dimethyl-4,9-dinitro-2,3,7,8-tetrachlorothianthrene,
1,9-dimethyl-4,6-dinitro-2,8-dibromothianthrene,
1,6-dimethyl-4,9-dinitro-2,7-dibromothianthrene,
1,9-diethyl-4,6-dinitrothianthrene,
1,6-diethyl-4,9-dinitrothianthrene,
2,4,6,8-tetranitrothianthrene,
2-acetylthianthrene,
2-trichloroacetyl-thianthrene,
2-trifluoroacetyl-thianthrene,
2,7-diacetylthianthrene,
2,8-diacetylthianthrene,
2,7-diacetyl-3,8-dichlorothianthrene,
2,7-diacetyl-1,3,6,8-tetrachlorothianthrene,
2-acetyl-7-trifluoroacetyl-thianthrene,
2-propionyl-3,7-dichlorothianthrene,
1,4-diacetyl-2,3,7,8-tetrachlorothianthrene,
2,7-dibenzoylthianthrene,
2,8-dibenzoylthianthrene,
2,7-dibenzoyl-3,8-dichlorothianthrene,
2,7-diacetyl-3,8-dicyanothianthrene,
1,4-dichloro-2-acetylthianthrene,
2,7-dinitro-3-trifluoroacetyl-thianthrene,
2,7-dibromo-2,8-bis(trifluoroacetyl)-thianthrene,
1-chloro-2-benzoyl-3,7-dibromothianthrene,
2,7-bis(acetoxy)-thianthrene,
2,7-dichloro-3,8-bis(acetyloxy)-thianthrene,
1,9-bis(trifluoroacetyloxy)-2,8-dichlorothianthrene,
2-benzoyloxythianthrene,
2-benzoyl-7-acetyl-3,8-dichlorothianthrene,
2-acetyloxy-1,3,6,7,8-pentachlorothianthrene,
2,7-bis(acetylamino)-thianthrene,
2,7-acetoy-3,8-dimethyl-1,4,6,9-tetrachlorothianthrene,
2,8-bis(acetylamino)-thianthrene
2,7-bis(acetylamino)-3,8-dichlorothianthrene,
2,8-bis(acetylamino)-1,3,7,9-tetrachlorothianthrene,
2-acetylamino-3,8-dicyano-6,7,9-trichlorothianthrene,
2-carboxylthianthrene,
2,7-dicarboxyl-3,8-dichlorothianthrene,
2,8-dicarboxyl-3,7-dichlorothianthrene,
2,7-bis(methoxycarbonyl)-thianthrene,
2,8-bis(methoxycarbonyl)-thianthrene,
1-methoxycarbonylthianthrene,
2-methoxycarbonylthianthrene,
2,7-bis(benzoylamino)-thianthrene,
2,8-bis(benzoylamino)-thianthrene,
2,7-bis(methoxycarbonyl)-3,8-dichlorothianthrene,
2,8-bis(methoxycarbonyl)-3,7-dichlorothianthrene,
2,7-bis(chlorocarbonyl)-thianthrene, 2,7-bis(fluorocarbonyl)-1,3,4,6,8,9-hexachlorothianthrene,
2,8-bis(bromocarbonyl)-thianthrene,
2,8-bis(chlorocarbonyl)-3,7-dichlorothianthrene,
2,7-bis(chlorocarbonyl)-3,8-dimethyl-1,4,6,9-tetrachlorothianthrene,
2,7-bis(methylthio)-thianthrene,
2,7-bis(phenylthio)-thianthrene,
2,7-bis(methylthio)-1,3,6,8-tetrachlorothianthrene,
2,7-bis(acetylthio)-thianthrene,
2,7-bis(acetylthio)-3,8-bis(methoxycarbonyl)-1,6-dichlorothianthrene,
2-benzoylthio-3,7,8-trichlorothianthrene,
2,7-disulphdthianthrene,
2,7-dichloro-3-sulphothianthrene,
2,8-disulpho-1,4,6,9-tetrachlorothianthrene,
2,7-bis(chlorosulphonyl)-thianthrene,
2,8-bis(chlorosulphonyl)-thianthrene,
2,7-bis(fluorosulphonyl)-thianthrene,
2,7-bis(chlorosulphonyl)-3,8-dichlorothianthrene,
2,8-bis(chlorosulphonyl)-3,7-dichlorothianthrene,
2,7-bis(chlorosulphonyl)-1,3,4,6,8,9-hexachlorothianthrene,
2-phenylsulphonyl-thianthrene,
2-tosylthianthrene,
2,7-ditosyl-3,8-dichlorothianthrene,
2,7-dimesyl-3,8-dichlorothianthrene,
2,7-bis(methoxysulphonyl)-3,8-dichlorothianthrene,
2,7-bis(phenoxysulphonyl)-1,3,6,9-tetrachlorothianthrene,
1,4,6,9-tetrachlorothianthrene-2,3,7,8-tetracarboxylic dianhydride,
1,4,6,9-tetrabromothianthrene-2,3,7,9-tetracarboxylic dianhydride,
cyclopentano[b]-thianthrene of the formula

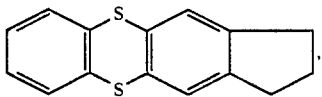

cyclohexano[b]-thianthrene of the formula

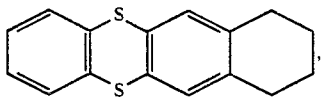

(diethyl-cyclopentano[b])-thianthrene of the formula

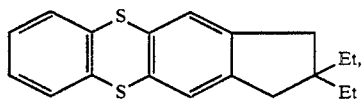

(diethyl-dioxo-cyclopentano[b])-thianthrene of the formula

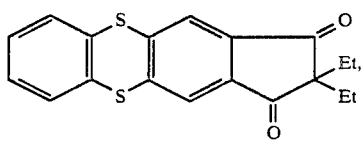

benzo[b]-thianthrene, 7,8-dichloro-benzo[b]-thianthrene,
thianthrene 5-oxide,
thianthrene 5,5-dioxide,
2,3,7,8-tetrachlorothianthrene 5-oxide,
2,7-dichlorothianthrene 5-oxide,
2,8-diamino-1,3,7,9-tetrachlorothianthrene, phenoxathiin,
2,8-dichlorophenoxathiin,
2,3,7,8-tetrachlorophenoxathiin,
1,2,3,7,8,9-hexachlorophenoxathiin,
1,2,3,6,7,8-hexachlorophenoxathiin,
2,3,4,6,7,7-hexachlorophenoxathiin,
octachlorophenoxathiin,
octafluorophenoxathiin,
2,8-difluorophenoxathiin,
2,3,7,8-tetrabromophenoxathiin,
2,8-difluoro-3,7-dichlorophenoxathiin,
2,8-dimethyl-1,3,7,9-tetrachlorophenoxathiin,
3,9-dimethyl-2,6,8-trichlorophenoxathiin,
3,6,9-trimethyl-8-chlorophenoxathiin,
3,6,9-trimethyl-1,2,4,7,8-pentachlorophenoxathiin,
2-methyl-1,3,7,8-tetrachlorophenoxathiin,
2,8-diethyl-1,3,7,9-tetrachlorophenoxathiin,
2-methoxy-1,3,7,8-tetrachlorophenoxathiin,
2,8-dimethyl-1,3,7,9-tetrabromophenoxathiin,
2,8-dimethyl-1,3,4,6,7,9-hexachlorophenoxathiin,
3,7-dimethyl-2,4,6,8-tetrachlorophenoxathiin,
1,7-dimethyl-2,4,8,9-tetrachlorophenoxathiin,
3,7-dimethyl-1,2,8,9-tetrachlorophenoxathiin,
4,6-dimethyl-2,3,7,8-tetrachlorophenoxathiin,
4,6-dimethyl-1,3,7,9-tetrachlorophenoxathiin,
2,8-diphenyl-1,3,7,9-tetrachlorophenoxathiin,
2,8-trifluoromethyl-3,7-dichlorophenoxathiin,
2,8-trifluoromethyl-1,3,7,9-tetrabromophenoxathiin,
2-benzyl-3,7,8-trichlorophenoxathiin,
2-methoxymethyl-3,7,9-trichlorophenoxathiin,
2,8-bis[(methoxycarbonyl)methyl]-1,3,7,9-tetrachlorophenoxathiin,
2-phenoxy-1,3,7,8-tetrachlorophenoxathiin,
2,8-dicyano-3,7-dichlorophenoxathiin,
1,4-dicyano-2,3,7,8-tetrachlorophenoxathiin,
2,3,7,8-tetracyanophenoxathiin,
2-nitro-1,4,7,8-tetrachlorophenoxathiin,
2-nitrophenoxathiin,
2,4-dinitro-7,8-dichlorophenoxathiin,
2,8-diacetyl-1,3,7,9-tetrachlorophenoxathiin,
2,8-bis(trifluoroacetyl)-3,7-dichlorophenoxathiin,
2,8-dibenzoyl-1,3,7,9-tetrachlorophenoxathiin,
2,8-dinitrophenoxathiin,
2,8-dinitro-3,7-dichlorophenoxathiin,
2,8-dinitro-3,7-dimethyl-1,9-dichlorophenoxathiin,
2-acetyl-1,3,7,8-tetrachlorophenoxathiin,
2,8-bis(acetylamino)-phenoxathiin,
2,8-bis(trifluoroacetylamino)-1,3,7,9-tetrachlorophenoxathiin,
2,8-bis(methoxycarbonyl)-1,3,7,9-tetrachlorophenoxathiin,
2-methoxycarbonyl-3,7-dichlorophenoxathiin,
2,8-bis(methoxycarbonyl)-1,3,6,9-tetrachlorophenoxathiin,
2,8-bis(chlorocarbonyl)-3,7-dichlorophenoxathiin,
2,8-bis(fluorocarbonyl)-3,7-dichlorophenoxathiin,
2,8-bis(chlorocarbonyl)-1,3,4,6,7,9-hexachlorophenoxathiin,
2,8-bis(methylthio)-1,3,7,9-tetrachlorophenoxathiin,
2,3-bis(acetylthio)-1,4,7,8-tetrachlorophenoxathiin,
2,8-bis(chlorosulphonyl)-3,7-dichlorophenoxathiin,
2,8-bis(chlorosulphonyl)phenoxathiin, 2,8-bis(chlorosulphonyl)-1,3,7,9-tetrachlorophenoxathiin,
2,8-bis(fluorosulphonyl)-3,7-dichlorophenoxathiin,
2,8-bis(chlorosulphonyl)-1,3,4,6,7,9-hexachlorophenoxathiin,
2,8-bismesyl-1,3,7-trichlorophenoxathiin, 2,8-bistosyl-1,3,7,9-tetrachlorophenoxathiin,
benzo[b]-8-nitro-phenoxathiin of the formula

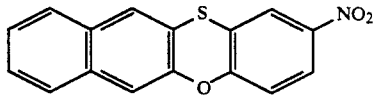

benzo[b]-1,4,6,9-tetrachloro-8-nitrophenoxathiin of the formula

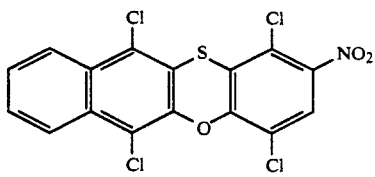

dibenzo[a,h]-3,8-dichloro-4,9-dibromophenoxathiin of the formula

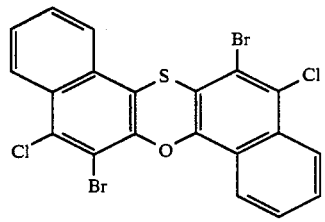

dibenzothiophene,
2,8-dichloro-dibenzothiophene,
2,3,7,8-tetrachloro-dibenzothiophene,
octachloro-dibenzothiophene,
2-bromo-dibenzothiophene,
2-nitro-dibenzothiophene,
2-nitro-7,8-dichloro-dibenzothiophene,
2-methoxy-3-nitro-dibenzohiophene,
2,8-difluoro-dibenzothiophene,
2,8-difluoro-3,7-dimethyl-dibenzothiophene,
2-acetylamino-dibenzothiophene,
2-acetylamino-3-nitro-dibenzothiophene,
2,3-dibromo-dibenzothiophene,
2,8-dibromo-dibenzothiophene,
2-phenylsulphonyl-dibenzothiophene,
2-phenylsulphonyl-3,7,8-trichloro-dibenzothiophene,
2,8-bis(chlorosulphonyl)-dibenzothiophene,
2-nitro-1,3,4,6,7,8,9-heptachloro-dibenzothiophene,
2-acetylamino-1,3,7,8-tetrachloro-dibenzothiophene,
2-carboxyl-1,3,7,8-tetrachloro-dibenzothiophene,
2-carboxyl-dibenzothiophene,
2-benzoyl-dibenzothiophene,
2-(2,4-dichlorobenzoyl)-dibenzothiophene,
3,7-diamino-2,4,6,8-tetrachloro-dibenzothiophene, octafluoro-dibenzothiophene.

The compounds of the formula (II) are fundamentally known to the person skilled in the art and can be prepared using known methods. Thus, phenoxathiins can be obtained by reaction of diaryl ethers with sulphur or with disulphur dichloride in the presence of aluminium chloride (Org. Synth., Coll. Vol. 2, p 485; J. Am. Chem. Soc. 59 (1937), 2578; EP-173 222; JP-A-56/110 630; J. Am. Chem. Soc. 58 (1936), 717; DE-AS 12 22 508; EP-63 384); a further preparation method consists in the ring closure of 2-sulphino-diaryl ethers (J. Chem. Soc. 123 (1923), 2876).

Thianthrenes can, for example, be prepared by reaction of aromatic compounds with sulphur or disulphur dichloride in the presence of aluminum chloride or by a condensation reaction of arylmercaptans in concentrated sulphuric acid or by ring closure of 2-sulphino-diaryl thioethers (Ann. 381 (1911), 312; J. Chem. Soc. 119 (1921), 1959; DE-OS 27 39 433; Ann. 407 (1915), 194; J. Chem. Soc. 123 (1923), 156).

Dibenzothiophenes can, for example, be obtained by reaction of biphenyls with sulphur or disulphur dichloride and aluminum chloride or from 2,2'-dihydroxybiphenyls and phosphorus pentasulphide (DE-PS 579 917, J. Org. Chem. 3 (1938), 108; DE-PS 330 833).

Such phenoxathiins, dibenzothiophenes or thianthrenes obtained by ring formation reactions can be converted still further into other derivatives using the known methods for substitution on aromatic rings, for example by chlorination, sulphochlorination, bromination, acylation and other reactions (J. Am. Chem. Soc. 58 (1936), 717; J. Am. Chem. Soc. 75 (1953), 3384; J. Chem. Soc. 1956, 2408; J. Am. Chem. Soc. 77 (1955), 5944; EP-173 222, EP-63 384; DE-OS 27 39 4333, DE-AS 12 22 508; Adv. Heterocycl. Chem. 16 (1974), 181).

Using the said preparation methods mixtures of positionally isomeric derivatives are often obtained. Thus, for example, in the synthesis of thianthrene from chlorobenzene, sulphur and AlCl3, 2,7-dichloro-thianthrene can be formed in a mixture with 2,8-dichloro-thianthrene in accordance with the following equation:

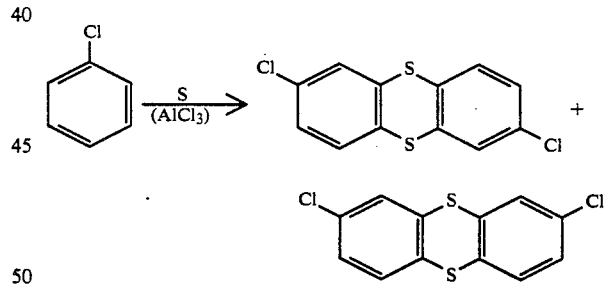

In a similar manner a mixture of 1-methyl- and 3-methyl-phenoxathiin is formed from 3-methyl-diphenyl ether, S2Cl2 and AlCl3, in accordance with the following equation:

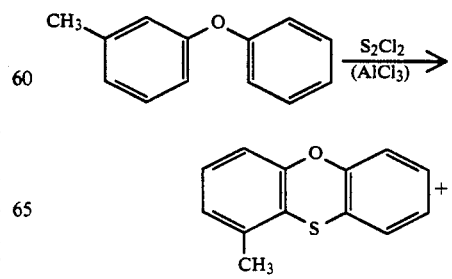

-continued

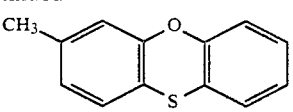

From other starting materials only one positionally isomeric product can be formed:

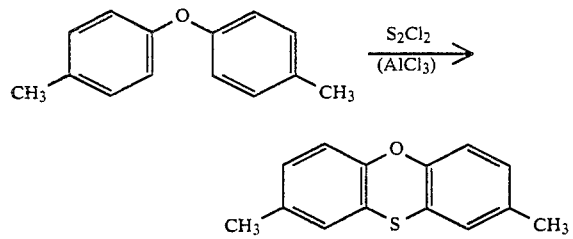

Mixtures of positionally isomeric products are also often obtained from the preparation of further derivatives of the heterocycles which are obtained by ring formation and can be used according to the invention. Thus, by chlorination of 2,8-dimethyl-phenoxathiin to an intermediate degree of chlorination of 4, a mixture is obtained which is mainly di-chlorinated in the two benzene rings, but in the conceivable different positional isomers; in addition, asymmetrically tetrachlorinated products are also formed (EP-63 384). Mixtures of tri-chlorinated and penta-chlorinated molecules can also result in an average degree of chlorination of 4.

Of course, when used in accordance with the invention such mixtures are absolutely equivalent to the pure compounds. For economic reasons such mixtures will even be used in preference, without separating them into the individual compounds. Furthermore cocatalysts that can be used in accordance with the invention are also those which form from compounds covered by the formula (II) only in the chlorination mixture on further chlorination. This group also includes, in addition to the ring-chlorinated compounds described, those compounds that contain sulphur-chlorine bonds and are, for example, formulated as thianthrene-dithionium chlorides.

Conversely, for example, it is also possible to use those thianthrene-dithionium chlorides or thianthrene-dithionium bromides which, in the context of an equilibrium, partially lose their chlorine (bromine) in the reaction mixture and are then partly present as compounds of the formula (II).

The co-catalysts which can be used according to the invention furthermore also include open-chain precursors which enter into a ring closure under the conditions according to the invention and are thus converted into co-catalysts according to the invention.

Preferably co-catalysts according to the invention of the formula

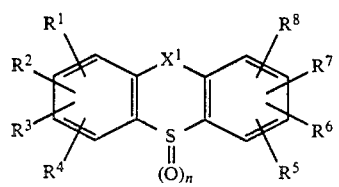

are used, in which
$X^1$ represents —O—, —S— or a single bond and
$R^1$ to $R^8$ and n have the meaning given above.

Further preferred co-catalysts that can be used in according to the invention are those of the formula

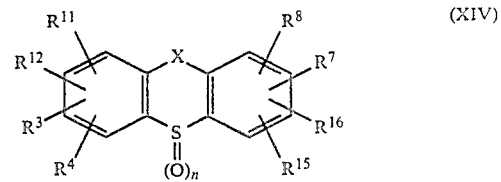

in which
$R^{11}$, $R^{12}$, $R^{15}$ and $R^{16}$ independently of one another denote hydrogen, halogen, cyano, nitro, halogenocarbonyl, halogenosulphonyl, $R^{19}$, $OR^{19}$, $COOR^{19}$ or $COR^{19}$,
$R^{19}$ representing straight-chain or branched $C_1$-$C_8$-alkyl, phenyl or benzyl,
and additionally two adjacent radicals $R^{11}$ and $R^{12}$ or $R^{15}$ and $R^{16}$ can represent a dicarboxylic anhydride group, and
$R^3$, $R^4$, $R^7$, $R^8$, X and n have the meaning given above.

Particularly preferred co-catalysts that can be used according to the invention are those of the formula

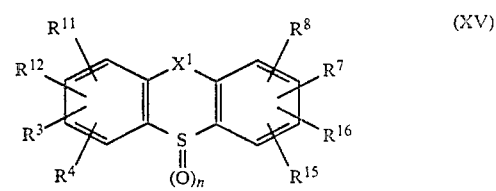

in which
$X^1$ represents —O—, —S— or a single bond and
$R^{11}$, $R^{12}$, $R^3$, $R^4$, $R^{15}$, $R^{16}$, $R^7$, $R^8$ and n have the meaning given above.

Further particularly preferred co-catalysts that can be used according to the invention are those of the formula

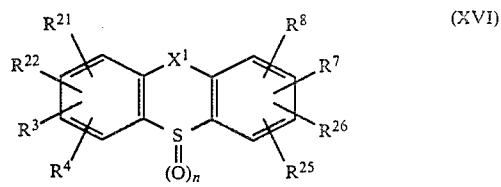

in which
$R^{21}$ and $R^{25}$ independently of one another denote hydrogen, fluorine, chlorine, bromine, cyano, nitro, fluorocarbonyl, chlorocarbonyl, chlorosulphonyl, $R^{29}$ or $OR^{29}$, $R^{29}$ representing straight-chain or branched $C_1$-$C_4$-alkyl, phenyl or benzyl,
$R^{22}$ and $R^{26}$ independently of one another denote hydrogen, fluorine, chlorine, bromine or straight-chain or branched $C_1$-$C_4$-alkyl,
and additionally adjacent radicals $R^{21}$ and $R^{22}$ jointly or $R^{25}$ and $R^{26}$ jointly can represent a dicarboxylic anhydride group, and
$R^3$, $R^4$, $R^7$, $R^8$, $X^1$ and n have the meaning given above.

Very particularly preferred co-catalysts that can be used according to the invention are those of the formula

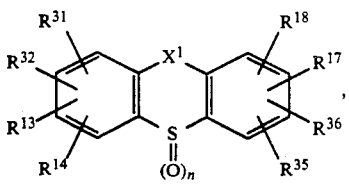

(XVII)

in which
and $R^{31}$ and $R^{35}$ independently of one another denote hydrogen, fluorine, chlorine, bromine, nitro, chlorocarbonyl, methyl, ethyl, methoxy, ethoxy or acetyl,
$R^{32}$ and $R^{36}$ independently of one another denote hydrogen, chlorine, bromine, methyl or ethyl,
and additionally adjacent radicals $R^{31}$ and $R^{32}$ jointly or $R^{35}$ and $R^{36}$ jointly can represent a dicarboxylic anhydride group,
$R^{13}$, $R^{14}$, $R^{17}$ and $R^{18}$ independently of one another denote hydrogen, chlorine, bromine, methyl, —CH$_2$—OCH$_3$ or —CH$_2$COOCH$_3$,
$X^1$ represents —O—, —S— or a single bond and
n assumes the value zero or one.

Further preferred co-catalysts are those of the formulae (XIII), (XV), (XVI) and (XVII), in which the ring member $X^2$ with the meaning —O— or —S— replaces $X^1$.

Of all the said compound classes, those in which the index n assumes the value zero are preferred.

Examples of the compounds of the formula (I) which, according to the invention, can be monochlorinated in the 2-position are: 4-nitro-toluene, 4-nitro-ethylbenzene, 4-nitro-propylbenzene and 4-nitro-butylbenzene; the process for the chlorination of 4-nitro-toluene is particularly important.

The process according to the invention is carried out in liquid phase, the 4-nitro-alkylbenzene (I) being used in the liquid (molten) form or, where appropriate, diluted with an inert solvent. Suitable solvents are those which are not attacked by chlorine or by the catalyst system under the conditions of the process according to the invention; such solvents are fundamentally known to the person skilled in the art and include, for example, methylene chloride, chloroform, carbon tetrachloride and acetic acid. The process is preferably carried out without solvent.

The chlorinating agent used for the process according to the invention is preferably chlorine, which is introduced into the reaction mixture in the liquid or gaseous form; gaseous chlorine is preferably introduced. However, other chlorinating agents which release chlorine under the reaction conditions can also be used, such as, for example, sulphuryl chloride.

The process according to the invention can in principle be carried out at a temperature from the solidification point to the boiling point of the reaction mixture. Generally the reaction temperature is 50°–150° C., preferably 70°–120° C. and particularly preferentially 80°–100° C. The reaction pressure can be atmospheric, reduced or elevated and is not critical in principle. The reaction is preferably carried out at atmospheric pressure because of the simplification of the reaction apparatus. An increase in the pressure can be indicated if a low-boiling reaction mixture (low-boiling solvent) is to be kept in the liquid phase. In this case the process is preferably carried out under the autogenous pressure automatically generated in such a reaction mixture.

The process according to the invention is intended for the preparation of a 2-chloro-4-nitroalkylbenzene, that is to say for the preparation of a monochlorinated compound. For such a monochlorination, 80–110 mole %, preferably 80–100 mole %, of chlorine in elemental form or in the form of a chlorine-releasing substance, are used per mole of 4-nitro-alkylbenzene.

In general it is not critical if the reaction mixture has a low water content. Therefore, in a preferred manner, none of the materials used need to be specially dried. Of course, such a complete drying of individual or all materials used is possible. A low water content is understood to mean a water content which is not above the saturation limits of the particular materials used. Furthermore, a low water content of this type may not be so large that the Friedel-Crafts catalyst used is completely consumed by hydrolysis. Examples which may be mentioned of low water contents in the reaction mixture are those up to 250 ppm, preferably up to 150 ppm.

Friedel-Crafts catalysts for the process according to the invention are all catalysts known to the person skilled in the art, such as antimony chlorides, aluminum chloride or iron chlorides. However, elements or compounds of elements can also be used which form a Friedel-Crafts catalyst (Lewis acid) during the chlorination. These include for example, the elements iron, antimony, aluminium or zinc, as well as the oxides, sulphides or carbonyls of these elements, and also salts of weak acids, such as the carbonates; examples which may be mentioned are antimony oxides, iron oxides, iron sulphides, iron carbonyls, iron carbonates or the like. The bromides, and possibly also the fluorides, of the said elements can also be used in place of the chlorides mentioned. Preferred Friedel-Crafts catalysts are antimony chlorides and iron chlorides, iron-III chloride is particularly preferred.

The amounts of the Friedel-Crafts catalyst, or of a mixture of several thereof, which are used can be varied within wide limits. Thus a catalyst effect is already detectable with an addition of 0.005% by weight. On the other hand, it is also possible to add 10% by weight or more of the Friedel-Crafts catalyst; however, in general, such high amounts offer no advantage, but are costly and may cause difficulties during working up. Customarily the Friedel-Crafts catalyst is used in an amount of 0.01–3% by weight, preferably of 0.05–1.5% by weight and particularly preferentially of 0.1–0.75% by weight. All amounts quoted are relative to the amount of 4-nitro-alkylbenzene used.

The co-catalysts according to the invention, or mixtures of several of these, or precursors mentioned can be used in an amount that can be varied within wide limits. However, with amounts of less than 0.01% by weight the co-catalytic effect decreases. Amounts above 10% by weight offer no further advantage, but are costly and can make working up more difficult. In general, the co-catalysts according to the invention are therefore used in amounts of 0.01–5% by weight, preferably 0.05–2.5% by weight and particularly preferentially 0.1–1% by weight, in each case relative to the 4-nitroalkylbenzene used.

In the process according to the invention the molar ratio of the Friedel-Crafts catalysts used to the cocatalysts can be varied within wide limits. In general it is advantageous to use the co-catalyst in not too large an excess and in not too large a deficit in relation to the Friedel-Crafts catalyst. In general, therefore, a molar ratio of Friedel-Crafts catalyst to co-catalyst of 50:1–1:10, preferably 10:1–1:2 and particularly preferentially 3:1–1:1.1 is chosen.

For carrying out the process according to the invention in practice, the sequence in which the individual components of the reaction mixture are added is arbitory. In this context the process can be carried out either continuously or discontinuously. The following is an exemplary embodiment:

The desired 4-nitro-alkylbenzene, for example 4-nitro-toluene, is initially introduced and heated, for example to 90° C. The desired amounts of Friedel-Crafts catalyst(s) and co-catalyst(s) are then added in any sequence and the preselected amount of gaseous chlorine is introduced whilst holding the temperature substantially constant. The mixture is then worked up in the customary manner, for instance by distillation.

The following is a further exemplary embodiment:

A solution of catalyst and co-catalyst in the desired 4-nitro-alkylbenzene is prepared and this solution is brought to the desired reaction temperature. A chlorinating agent is then added in the intended amount. Here also the working up can be carried out by distillation.

The process according to the invention is marked by a pronounced stage-selectivity in respect of the monochlorination. Furthermore the use, according to the invention, of the co-catalysts described above is marked by an activating effect on the course of the chlorination, so that the losses due to non-reacted chlorine leaving the reaction mixture again are substantially reduced. It did not appear possible to combine this activation with a selectivity in respect of a monochlorination. It is furthermore also surprising that these good results are achieved at an industrially very advantageous temperature in the abovementioned range.

Furthermore the fact that the co-catalysts according to the invention, in particular with the industrially exceptionally favourable and desirable Friedel-Crafts catalyst iron-III chloride, produce the good results mentioned is also advantageous.

In the following exemplary embodiments the selectivity for the formation of the 2-chloro-4-nitroalkylbenzene is defined as follows:

$$\text{Selectivity} = \frac{[\text{2-Cl-4-NO}_2\text{-alkylbenzene content}]}{100 - [\text{residual 4-NO}_2\text{-alkylbenzene content}]} \times 100(\%)$$

This selectivity indicates the percentage to which the unreacted 4-nitro-alkylbenzene has been converted into the desired 2-chloro-4-nitro-alkylbenzene.

The chlorine loss is defined as follows:

$$\text{Chlorine loss} = \frac{[\text{mass of the Cl}_2 \text{ which has left the reaction mixture}]}{[\text{mass of the Cl}_2 \text{ introduced}]} \times 100(\%)$$

The chlorine loss indicates the percentage of the chlorine passed through the solution which has remained unused and passes into the exhaust gas.

EXAMPLE 1

Preparation of further chlorinated co-catalysts 1.0 mole of the co-catalyst or co-catalyst mixture to be further chlorinated, for example, 200 g of phenoxathiin, were suspended in 2,000 g of perchloroethylene and the suspension was heated to 100° C. with 3.5 g of FeCl$_3$. Gaseous chlorine was passed in slowly, with stirring, until the desired degree of chlorination was reached, for example 4.0 mole $\triangleq$ 284 g of chlorine over 8 h until a degree of chlorination of 4.0 is reached. The perchloroethylene was removed by vacuum distillation and the residue was recrystallized or reprecipitated, for example from perchloroethylene/methanol. After drying at elevated temperature, for example 100° C. under vacuum, the degree of chlorination was checked by elementary analysis, for example for the phenoxathiin prepared in this manner with a degree of chlorination of 4.0, the following analysis values were obtained (duplicate determination):

|   | Found       | Calculated for $C_{12}H_4Cl_4OS$ |
|---|-------------|----------------------------------|
| C | 42.7/42.6%  | 42.64%                           |
| H | 1.3/1.3%    | 1.19%                            |
| Cl| 42.2/42.0%  | 41.95%                           |
| S | 9.6/9.4%    | 9.49%                            |

EXAMPLES 2–28

In order to ensure flawless comparison of the selectivity and yield and of the chlorine loss all chlorination examples were carried out under the following constant reaction conditions: reaction temperature 90° C.±2° C.; amount of chlorine 97–100 mole %, relative to p-alkyl-nitrobenzene, gaseous; period of the Cl$_2$ introduction 5 hours at a steady rate of Cl$_2$ addition.

EXAMPLE 2 for comparison; chlorination with iron-III chloride 100 parts by weight of 4-nitrotoluene were initially introduced into a reactor and 0.6 part by weight of iron-III chloride were added. The mixture was chlorinated under the abovementioned conditions. The residual 4-nitrotoluene content was 10.3% by weight and the selectivity for the formation of 2-chloro-4-nitrotoluene was 92.7%. The chlorine loss was 5.5% of the chlorine introduced.

EXAMPLE 3 for comparison; chlorination with iron-III chloride and iodine as co-catalyst 100 parts by weight of 4-nitrotoluene were initially introduced into a reactor and 0.6 part by weight of iron-III chloride and 0.03 part by weight of the co-catalyst elemental iodine were added and the mixture was chlorinated as described. The residual 4-nitrotoluene content was 8.7% by weight and the selectivity for the formation of 2-chloro-4-nitrotoluene was 96.8%. The chlorine loss was 6.6% of the chlorine introduced. Iodine could be detected in the reaction product.

EXAMPLE 4

100 parts by weight of 4-nitrotoluene were initially introduced into a reactor and 0.3 part by weight of iron-III chloride and 0.528 part by weight of the co-catalyst of the formula

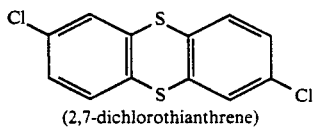

(2,7-dichlorothianthrene)

were added and the mixture was chlorinated as described. The residual 4-nitrotoluene content was 5.9% by weight and the selectivity for the formation of 2-chloro-4-nitrotoluene was 98.3%. The chlorine loss was 3.4% of the chlorine introduced.

EXAMPLE 5

100 parts by weight of 4-nitrotoluene were initially introduced into a reactor and 0.15 part by weight of iron-III chloride and 0.339 part by weight of the co-catalyst mixture of the formula

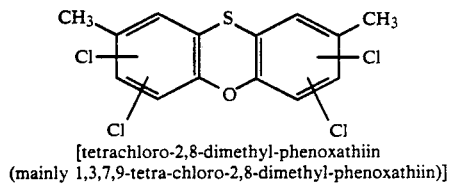

[tetrachloro-2,8-dimethyl-phenoxathiin
(mainly 1,3,7,9-tetra-chloro-2,8-dimethyl-phenoxathiin)]

that had been prepared according to Example 1 by chlorinating

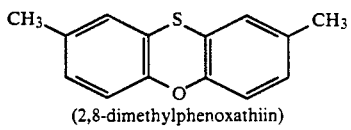

(2,8-dimethylphenoxathiin)

upto the average degree of chlorination of 4.0, were added and the mixture was chlorinated as described. The residual 4-nitrotoluene content was 2.9% by weight and the selectivity for the formation of 2-chloro-4-nitrotoluene was 98.1%. The chlorine loss was 0.8% of the chlorine introduced.

EXAMPLE 6

100 parts by weight of 4-nitrotoluene were initially introduced into a reactor and 0.152 part by weight of iron-III chloride and 0.344 part by weight of the co-catalyst mixture of the formula

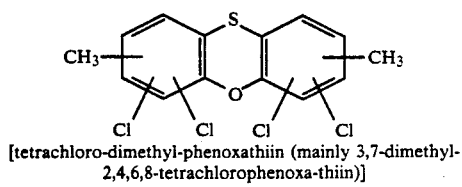

[tetrachloro-dimethyl-phenoxathiin (mainly 3,7-dimethyl-2,4,6,8-tetrachlorophenoxa-thiin)]

were added and the mixture was chlorinated as described. The co-catalyst mixture had been prepared according to Example 1 by chlorinating of a mixture of

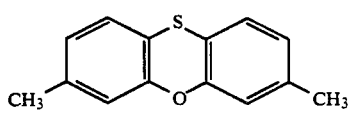

3,7-dimethylphenoxathiin and

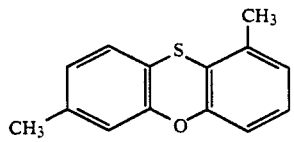

1,7-dimethylphenoxathiin, that for its part had been prepared from 3,3'-dimethyl-diphenyl ether, sulphur and AlCl₃, upto the average degree of chlorination of 4.0. The residual 4-nitrotoluene content was 4.3% by weight and the selectivity for the formation of 2-chloro-4-nitrotoluene was 98.4%. The chlorine loss was 3.0% of the chlorine introduced.

EXAMPLE 7

100 parts by weight of 4-nitrotoluene were initially introduced into a reactor and 0.152 part by weight of iron-III chloride and 0.318 part by weight of the co-catalyst mixture of the formula

(tetrachlorophenoxathiin)

that had been prepared in accordance with Example 1 by chlorinating

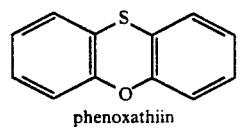

phenoxathiin upto the average degree of chlorination of 4.0, were added and the mixture was chlorinated as described. The residual 4-nitrotoluene content was 5.3% by weight and the selectivity for the formation of 2-chloro-4-nitrotoluene was 98.7%. The chlorine loss was 3.% of the chlorine introduced.

EXAMPLE 8

100 parts by weight of 4-nitrotoluene were initially introduced into a reactor and 0.15 part by weight of iron-III chloride and 0.446 part by weight of the co-catalyst of the formula

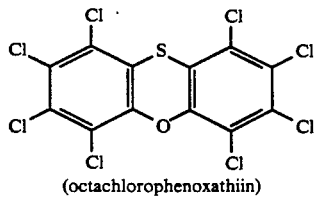

(octachlorophenoxathiin)

were added and the mixture was chlorinated as described. The residual 4-nitrotoluene content was 3.4% by weight and the selectivity for the formation of 2-chloro-4-nitrotoluene was 98.1%. The chlorine loss was 0.7% of the chlorine introduced.

EXAMPLE 9

100 parts by weight of 4-nitrotoluene were initially introduced into a reactor and 0.301 part by weight of iron-III chloride and 0.402 part by weight of the co-catalyst of the formula

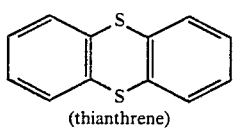

(thianthrene)

were added and the mixture was chlorinated as described. The residual 4-nitrotoluene content was 6.9% by weight and the selectivity for the formation of 2-chloro-4-nitrotoluene was 98.1%. The chlorine loss was 3.7% of the chlorine introduced.

EXAMPLE 10

100 parts by weight of 4-nitrotoluene were initially introduced into a reactor and 0.301 part by weight of iron-III chloride and 0.558 part by weight of the co-catalyst of the formula

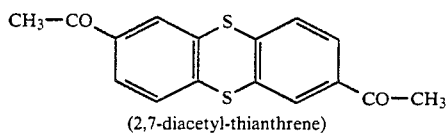

(2,7-diacetyl-thianthrene)

were added and the mixture was chlorinated as described. The residual 4-nitrotoluene content was 9.3% by weight and the selectivity for the formation of 2-chloro-4-nitrotoluene was 98.1%. The chlorine loss was 5.2% of the chlorine introduced.

EXAMPLE 11

100 parts by weight of 4-nitrotoluene were initially introduced into a reactor and 0.30 part by weight of iron-III chloride and 0.67 part by weight of the co-catalyst of the formula

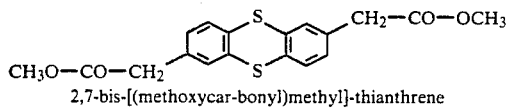

2,7-bis-[(methoxycar-bonyl)methyl]-thianthrene were added and the mixture was chlorinated as described. The residual 4-nitrotoluene content was 5.9% by weight and the selectivity for the formation of 2-chloro-4-nitrotoluene was 98.1%. The chlorine loss was 1.9% of the chlorine introduced.

EXAMPLE 12

100 parts by weight of 4-nitrotoluene were initially introduced into a reactor and 0.301 part by weight of iron-III chloride and 0.915 part by weight of the co-catalyst of the formula

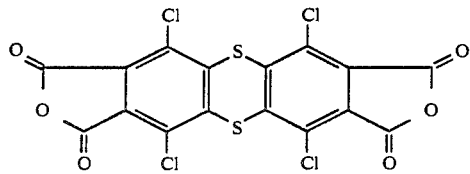

(1,4,6,9-tetrachlorothianthrene-2,3,7,8-tetracarboxylic dianhydride)

were added and the mixture was chlorinated as described. The residual 4-nitrotoluene content was 4.3% by weight and the selectivity for the formation of 2-chloro-4-nitrotoluene was 96.7%. The chlorine loss was 2.0% of the chlorine introduced.

EXAMPLE 13

100 parts by weight of 4-nitrotoluene were initially introduced into a reactor and 0.15 part by weight of iron-III chloride and 0.49 part by weight of the co-catalyst of the formula

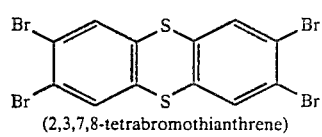

(2,3,7,8-tetrabromothianthrene)

were added and the mixture was chlorinated as described. The residual 4-nitrotoluene content was 6.8% by weight and the selectivity for the formation of 2-chloro-4-nitrotoluene was 97.4%. The chlorine loss was 4.1% of the chlorine introduced.

EXAMPLE 14

100 parts by weight of 4-nitrotoluene were initially introduced into a reactor and 0.301 part by weight of iron-III chloride and 0.712 part by weight of the co-catalyst mixture of the formula

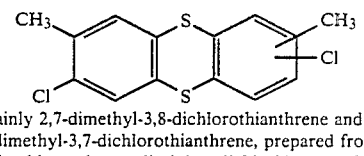

(mainly 2,7-dimethyl-3,8-dichlorothianthrene and 2,8-dimethyl-3,7-dichlorothianthrene, prepared from orthochlorotoluene, disulphur dichloride and AlCl₃), were added and the mixture was chlorinated as described. The residual 4-nitrotoluene content was 6.6% by weight and the selectivity for the formation of 2-chloro-4-nitrotoluene was 98.1%. The chlorine loss was 5.0% of the chlorine introduced.

EXAMPLE 15

100 parts by weight of 4-nitrotoluene were initially introduced into a reactor and 0.3 part by weight of iron-III chloride and 0.429 part by weight of the co-catalyst of the formula

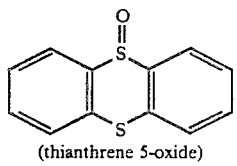

(thianthrene 5-oxide)

were added and the mixture was chlorinated as described. The residual 4-nitrotoluene content was 8.5% by weight and the selectivity for the formation of 2-chloro-4-nitrotoluene was 96.5%. The chlorine loss was 6.7% of the chlorine introduced.

EXAMPLE 16

100 pats by weight of 4-nitrotoluene were initially introduced into a reactor and 0.301 part by weight of iron-III chloride and 0.549 part by weight of the co-catalyst of formula

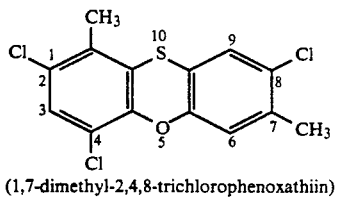

(1,7-dimethyl-2,4,8-trichlorophenoxathiin)

were added and the mixture was chlorinated as described. The residual 4-nitrotoluene content was 5.9% by weight and the selectivity for the formation of 2-chloro-4-nitrotoluene was 98.5%. The chlorine loss was 3.8% of the chlorine introduced.

EXAMPLE 17

100 parts by weight of 4-nitrotoluene were initially introduced into a reactor and 0.15 part by weight of iron-III chloride and 0.42 part by weight of the cocatalyst mixture of the formula

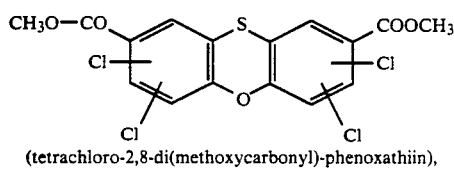

(tetrachloro-2,8-di(methoxycarbonyl)-phenoxathiin), that had been prepared according to Example 1 by chlorinating

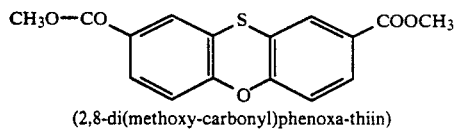

(2,8-di(methoxy-carbonyl)phenoxa-thiin)

upto the average degree of chlorination of 4.0, were added and the mixture was chlorinated as described. The residual 4-nitrotoluene content was 2.5% by weight and the selectivity for the formation of 2-chloro-4-nitrotoluene was 97.6%. The chlorine loss was 0.5% of the chlorine introduced.

EXAMPLE 18

100 parts by weight of 4-nitrotoluene were initially introduced into a reactor and 0.151 part by weight of iron-III chloride and 0.283 part by weight of the co-catalyst mixture of the formula,

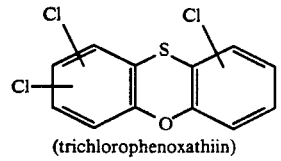

(trichlorophenoxathiin)

that had been prepared according to Example 1 by chlorinating

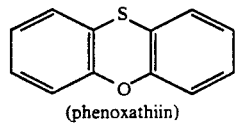

(phenoxathiin)

upto the average degree of chlorination of 3.0, were added and the mixture was chlorinated as described. The residual 4-nitrotoluene content was 6.0% by weight and the selectivity for the formation of 2-chloro-4-nitrotoluene was 98.0%. The chlorine loss was 5.3% of the chlorine introduced.

EXAMPLE 19

100 parts by weight of 4-nitrotoluene were initially introduced into a reactor and 0.3 part by weight of iron-III chloride and 0.69 part by weight of the co-catalyst mixture of the formula

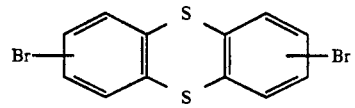

(mainly 2,7-dibromothianthrene and 2,8-dibromothianthrene), prepared by reaction of 1 mole of thianthrene with 2 moles of $Br_2$ in boiling glacial acetic acid, were added and the mixture was chlorinated as described. The residual 4-nitrotoluene content was 6.8% by weight and the selectivity for the formation of 2-chloro-4-nitrotoluene was 97.5%. The chlorine loss was 3.4% of the chlorine introduced.

EXAMPLE 20

100 parts by weight of 4-nitrotoluene were initially introduced into a reactor and 0.3 part by weight of iron-III chloride and 0.469 part by weight of the co-catalyst of the formula

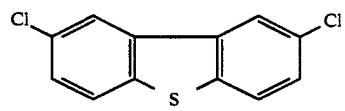

(2,8-dichloro-dibenzothiophene)

were added and the mixture was chlorinated as described. The residual 4-nitrotoluene content was 7.4% by weight the selectivity for the formation of 2-chloro-4-nitrotoluene was 98.4%. The chlorine loss was 2.9% of the chlorine introduced.

EXAMPLE 21

100 parts by weight of 4-nitro-ethylbenzene were initially introduced into a reactor and 0.138 part by weight of iron-III chloride and 0.311 part by weight of the co-catalyst mixture of the formula,

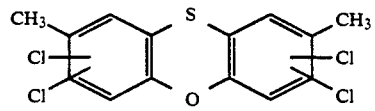

-continued
[tetrachloro-2, 8-dimethylphenoxathiin, (mainly 1,3,7,9-tetrachloro-2, 8-dimethylphenoxathiin)], that had been prepared according to Example 1 by chlorinating

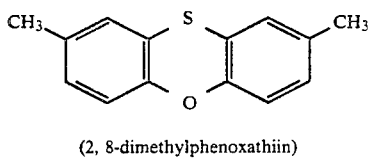

(2, 8-dimethylphenoxathiin)

upto the average degree of chlorination of 4.0, were added and the mixture was chlorinated as described. The residual 4-nitro-ethylbenzene content was 8.3% by weight and the selectivity for the formation of 2-chloro-4nitrotoluene was 97.0%. The chlorine loss was 2.6% of the chlorine introduced.

EXAMPLE 22

100 parts by weight of 4-nitrotoluene were initially introduced into a reactor and 0.300 part by weight of iron-III chloride and 0.656 part by weight of the co-catalyst mixture of the formula

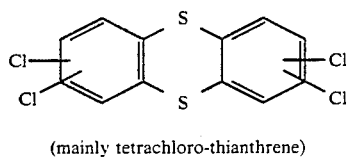

(mainly tetrachloro-thianthrene)

that had been, prepared according to Example 1 by chlorinating

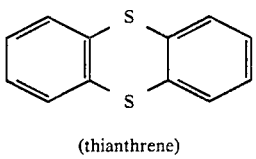

(thianthrene)

upto the average degree of chlorination of 4.1, were added and the mixture was chlorinated as described. The residual 4-nitrotoluene content was 5.8% by weight and the selectivity for the formation of 2-chloro-4-nitrotoluene was 98.0%. The chlorine loss was 2.7% of the chlorine introduced.

EXAMPLE 23

100 parts by weight of 4-nitrotoluene were initially introduced into a reactor and 0.301 part by weight of iron-III chloride and 0.513 part by weight of the co-catalyst of the formula

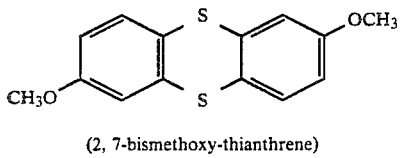

(2, 7-bismethoxy-thianthrene)

were added and the mixture was chlorinated as described. The residual 4-nitrotoluene content was 8.4% by weight and the selectivity for the formation of 2-chloro-4nitrotoluene was 97.0%. The chlorine loss was 4.5% of the chlorine introduced.

EXAMPLE 24

100 parts by weight of 4-nitrotoluene were initially introduced into a reactor and 0.30 part by weight of iron-III chloride and 0.46 part by weight of the co-catalyst of the formula

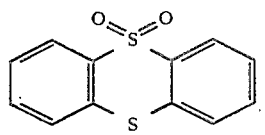

(thianthrene 5, 5-dioxide)

were added and the mixture was chlorinated as described. The residual 4-nitrotoluene content was 6.8% by weight and the selectivity for the formation of 2-chloro-4-nitrotoluene was 98.4%. The chlorine loss was 4.4% of the chlorine introduced.

EXAMPLE 25

100 parts by weight of 4-nitrotoluene were initially introduced into a reactor and 0.300 part by weight of iron-III chloride and 0.480 part by weight of the co-catalyst of the formula

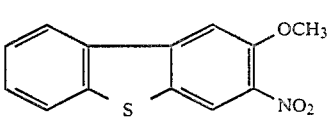

(2-methoxy-3-nitrodi-benzothiophene)

were added and the mixture was chlorinated as described. The residual 4-nitrotoluene content was 8.3% by weight and the selectivity for the formation of 2-chloro-4nitrotoluene was 96.6%. The chlorine loss was 5.2% of the chlorine introduced.

EXAMPLE 26

100 parts by weight of 4-nitrotoluene were initially introduced into a reactor and 0.15 part by weight of iron-III chloride and 0.34 part by weight of the co-catalyst mixture of the formula

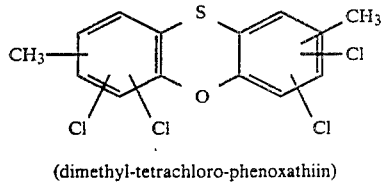

(dimethyl-tetrachloro-phenoxathiin)

were added and the mixture was chlorinated as described. The co-catalyst mixture had been prepared according to Example 1 by chlorinating a mixture of

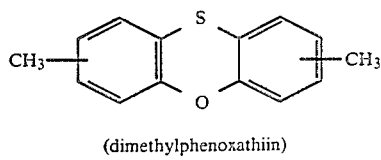

(dimethylphenoxathiin)

that for its part had been prepared from a technical grade mixture of all possible isomeric ditolyl ethers, sulphur and AlCl$_3$, up to the average degree of chlorination of 4.1.

The residual 4-nitrotoluene content was 4.9% by weight and the selectivity for the formation of 2-chloronitrotoluene was 98.5%. The chlorine loss was 3.4% of the chlorine introduced.

EXAMPLE 27

100 parts by weight of 4-nitrotoluene were initially introduced into a reactor and 0.300 part by weight of iron-III chloride and 0.580 part by weight of the co-catalyst of the formula

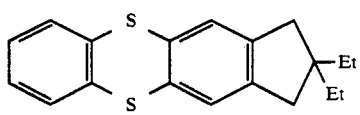

(diethyl-cyclopen-tano [6])-thianthrene were added and the mixture was chlorinated as described. The residual 4-nitrotoluene content was 6.9% by weight and the selectivity for the formation of 2-chloro-4-nitrotoluene was 98.3%. The chlorine loss was 2.8% of the chlorine introduced.

EXAMPLE 28

100 parts by weight of 4-nitrotoluene were initially introduced into a reactor and 0.301 part by weight of iron-III chloride and 0.656 part by weight of the co-catalyst mixture of the formula

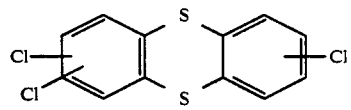

(mainly trichlorothianthrene)

that had been prepared according to Example 1 by chlorinating

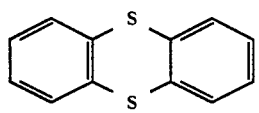

(thianthrene)

up to the average degree of chlorination of 3.2, were added and the mixture was chlorinated as described. The residual 4-nitrotoluene content was 7.6% by weight and the selectivity for the formation of 2-chloro-4-nitrotoluene was 98.3%. The chlorine loss was 4.8% of the chlorine introduced.

What is claimed is:

1. A process for the preparation of 2-chloro-4-nitroalkylbenzene of the formula

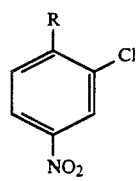

in which

R represents $C_1$-$C_4$-alkyl, by reaction of the 4-nitro-alkylbenzene on which the product is based, with elemental chlorine or chlorine-releasing compounds in the presence of a Friedel-Crafts catalyst and a co-catalyst in the liquid phase, characterized in that the co-catalyst used is a dibenzo-condensed sulphur heterocycle of the formula

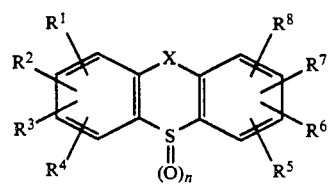

in which $R^1$, $R^2$, $R^5$ and $R^6$ independently of one another denote hydrogen, halogen, hydroxy, cyano, nitro, amino, carboxyl, halogenocarbonyl, the sulphonic acid group, halogenosulphonyl, $R^9$, $OR^9$, $SR^9$, $COR^9$, $OCOR^9$, $COOR^9$, $NHCOR^9$, $SCOR^9$, $SO_2R^9$ or $SO_2$—$OR^9$, $R^9$ representing straight-chain or branched $C_1$-$C_8$-alkyl, $C_5$-$C_8$-cycloalkyl, $C_6$-$C_{12}$-aryl or $C_7$-$C_{10}$-aralkyl, $R^3$, $R^4$, $R^7$ and $R^8$ independently of one another and of the above radicals denote hydrogen, halogen or straight-chain or branched $C_1C_8$-alkyl, or $C_1$-$C_8$-alkyl interrupted by the ether group —O— or by the ester group —OCO—, and additionally two adjacent radicals of $R^1$ to $R^4$ or of $R^5$ to $R^8$ can jointly form a fused ring, which can have 5 to 8 ring members and can be saturated, unsaturated, aromatic or, with the inclusion of one or two atoms from the group N, O and S, heterocyclic, and, furthermore two adjacent radicals $R^1$ and $R^2$ or $R^5$ and $R^6$ can represent a dicarboxylic anhydride group, X represents —O—, —S—, —SO—, —SO$_2$— or a single bond and n assumes the value zero or one.

2. The process of claim 1, wherein a co-catalyst of the formula

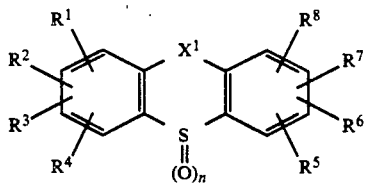

is used, in which $X^1$ represents —O—, —S— or a single bond and $R^1$ to $R^8$ and n have the meaning given in claim 1.

3. The process of claim 1, wherein a co-catalyst of the formula

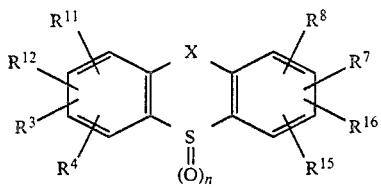

is used, in which

R[11], R[12], R[15] and R[16] independently of one another denote hydrogen, halogen, cyano, nitro, halogenocarbonyl, halogenosulphonyl, R[19], OR[19], —COOR[19] or COR[19], R[19] representing straight-chain or branched $C_1$-$C_8$-alkyl, phenyl or benzyl, and additionally two adjacent radicals R[11] and R[12] or R[15] and R[16] can represent a dicarboxylic anhydride group, and R[3], R[4], R[7], R[8], X and n have the meaning given in claim 1.

4. The process of claim 3, wherein a co-catalyst of the formula

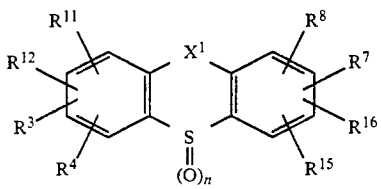

is used, in which

X[1] represents —O—, —S— or a single bond and

R[11], R[12], R[3], R[4], R[15], R[16], R[7], R[8] and n have the meaning given in claim 3.

5. The process of claim 4, wherein a co-catalyst of the formula

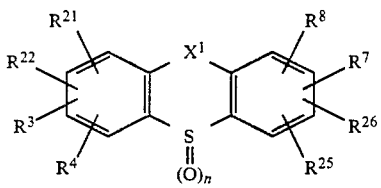

is used, in which

R[21] and R[25] independently of one another denote hydrogen, fluorine, chlorine, bromine, cyano, nitro, fluorocarbonyl, chlorocarbonyl, chlorosulphonyl, R[29] or OR[29], R[29] representing straight-chain or branched $C_1$-$C_4$-alkyl, phenyl or benzyl, R[22] and R[26] independently of one another denote hydrogen, fluorine, chlorine, bromine or straight-chain or branched $C_1$-$C_4$-alkyl,
  and additionally adjacent radicals R[21] and R[22] jointly or R[25] and R[26] jointly can represent a dicarboxylic anhydride group, and R[3], R[4], R[7], R[8], X[1] and n have the meaning given in claim 4.

6. The process of claim 5, wherein a co-catalyst of the formula

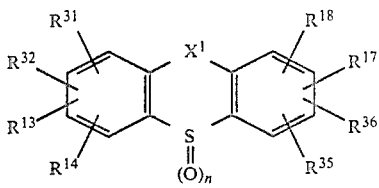

is used, in which

R[31] and R[35] independently of one another denote hydrogen, fluorine, chlorine, bromine, nitro, chlorocarbonyl, methyl, ethyl, methoxy, ethoxy or acetyl, R[32] and R[36] independently of one another denote hydrogen, chlorine, bromine, methyl or ethyl,
  and additionally adjacent radicals R[31] and R[32] jointly or R[35] and R[36] jointly can represent a dicarboxylic anhydride group, R[13], R[14], R[17] and R[18] independently of one another denote hydrogen, chlorine, bromine, methyl, —CH$_2$—OCH$_3$ or —CH$_2$COOCH$_3$, X[1] represents —O—, —S— or a single bond and n assumes the value zero or one.

7. The process of claim 2 wherein the ring member X[2] with the meaning —O— or —S— replaces X[1].

8. The process of claim 1, wherein 80-110 mole % of chlorine in elemental form or in the form of a chlorine-releasing substance are used per mole of 4-nitro-alkylbenzene.

9. The process of claim 8, wherein 80-100 mole % of chlorine in elemental form or in the form of a chlorine-releasing substance are used per mole of 4-nitro-alkylbenzene.

10. The process of claim 1, wherein the Friedel-Crafts catalyst is used in an amount of 0.005-10% by weight relative to the amount of 4-nitro-alkylbenzene.

11. The process of claim 10, wherein the Friedel-Crafts catalyst is used in an amount of 0.01 to 3% by weight, relative to the amount of 4-nitro-alkylbenzene.

12. The process claim 11, wherein the Friedel-Crafts catalyst is used in an amount of 0.05-1.5% by weight, relative to the amount of 4-nitro-alkylbenzene.

13. The process of claim 1, wherein the co-catalyst or a mixture of several of these is used in an amount of 0.01-10% by weight, relative to the amount of 4-nitroalkylbenzene.

14. The process of claim 13, wherein the co-catalyst or a mixture of several of these is used in an amount of 0.01-5% by weight, relative to the amount of 4-nitroalkylbenzene.

15. The process of claim 14, wherein the co-catalyst or a mixture of several of these is used in an amount of 0.05-2.5% by weight, relative (o the amount of 4-nitroalkylbenzene.

16. The process of claim 15, wherein the co-catalyst or a mixture of several of these is used in an amount of 0.1-1% by weight, relative to the amount of 4-nitroalkylbenzene.

17. The process of claim 1, wherein the molar ratio of Friedel-Crafts catalyst to co-catalyst is adjusted in the range of 50:1-1:10.

18. The process of claim 17, wherein the molar ratio of Friedel-Crafts catalyst to co-catalyst is adjusted in the range of 10:1-1:2.

19. The process of claim 18, wherein the molar ratio of Friedel-Crafts catalyst o co-catalyst is adjusted in the range of 3:1-1:1.1.

20. The process of claim 1, wherein the chlorinating agent used is chlorine in the liquid or gaseous form.

* * * * *